(12) United States Patent
Robie et al.

(10) Patent No.: US 7,749,272 B2
(45) Date of Patent: Jul. 6, 2010

(54) PROSTHETIC DISC AND VERTEBRAL BODY REPLACEMENT DEVICE HAVING PYROLYTIC CARBON BEARING MEMBERS

(75) Inventors: Bruce H. Robie, Glen Rock, NJ (US); Eric Woodard, Jamaica Plains, MA (US)

(73) Assignee: Zimmer Trabecular Metal Technology, Inc., Allendale, NJ (US)

( * ) Notice: Subject to any disclaimer, the term of this patent is extended or adjusted under 35 U.S.C. 154(b) by 453 days.

(21) Appl. No.: 11/656,766

(22) Filed: Jan. 23, 2007

(65) Prior Publication Data

US 2007/0118221 A1 May 24, 2007

Related U.S. Application Data

(63) Continuation of application No. 10/264,496, filed on Oct. 4, 2002, now abandoned.

(51) Int. Cl.
*A61F 2/44* (2006.01)
*A61F 2/02* (2006.01)

(52) U.S. Cl. .................... 623/17.11; 623/23.72

(58) Field of Classification Search ... 623/17.15–17.16, 623/23.72, 23.73, 23.74
See application file for complete search history.

(56) References Cited

U.S. PATENT DOCUMENTS

| | | | | |
|---|---|---|---|---|
| 3,685,059 A | * | 8/1972 | Bokros et al. | 623/2.42 |
| 3,707,006 A | * | 12/1972 | Bokros et al. | 424/422 |
| 3,971,134 A | * | 7/1976 | Bokros | 433/201.1 |
| 4,166,292 A | * | 9/1979 | Bokros | 623/21.18 |
| 5,071,437 A | * | 12/1991 | Steffee | 623/17.16 |
| 5,084,151 A | * | 1/1992 | Vallana et al. | 204/192.11 |
| 5,133,845 A | * | 7/1992 | Vallana et al. | 204/192.15 |
| 5,282,861 A | | 2/1994 | Kaplan | |
| 5,522,886 A | * | 6/1996 | Milo | 623/2.31 |
| 5,645,605 A | * | 7/1997 | Klawitter | 623/21.15 |
| 5,683,464 A | | 11/1997 | Wagner et al. | |
| 5,716,400 A | * | 2/1998 | Davidson | 623/2.42 |
| 5,861,041 A | * | 1/1999 | Tienboon | 623/17.16 |
| 5,899,939 A | * | 5/1999 | Boyce et al. | 623/16.11 |
| 6,183,517 B1 | * | 2/2001 | Suddaby | 623/17.16 |
| 6,290,726 B1 | * | 9/2001 | Pope et al. | 623/22.15 |
| 6,375,655 B1 | * | 4/2002 | Zdeblick et al. | 623/17.16 |
| 6,410,087 B1 | * | 6/2002 | Wilde et al. | 427/249.1 |
| 6,419,705 B1 | * | 7/2002 | Erickson | 623/17.16 |
| 6,554,863 B2 | * | 4/2003 | Paul et al. | 623/17.11 |
| 6,569,201 B2 | * | 5/2003 | Moumene et al. | 623/17.11 |
| 6,607,558 B2 | | 8/2003 | Kuras | |
| 6,626,945 B2 | | 9/2003 | Simon et al. | |
| 6,726,718 B1 | * | 4/2004 | Carlyle et al. | 623/2.42 |

(Continued)

OTHER PUBLICATIONS

"Wear Characteristics of the Canine Acetabulum Against Different Femoral Prostheses", Stephen D. Cook et al., 1989 British Editorial Society of Bone and Joint Surgery, vol. 71-B, No. 2, Mar. 1989, pp. 189-197.

*Primary Examiner*—Alvin J Stewart
(74) *Attorney, Agent, or Firm*—Crompton, Seager & Tufte, LLC (57) ABSTRACT

A spinal motion device for implanting in the spine as a replacement for the natural disc, to permit motion between adjacent vertebral bodies or as a vertebral body replacement that permits motion at its ends. The spinal motion device comprises a composite structure formed by a body having at least one bearing member, made from a biocompatible material such as pyrolytic carbon, attached to a support surface thereof.

23 Claims, 6 Drawing Sheets

U.S. PATENT DOCUMENTS

| | | | |
|---|---|---|---|
| 6,726,720 B2 * | 4/2004 | Ross et al. | 623/17.13 |
| 7,250,060 B2 * | 7/2007 | Trieu | 623/17.15 |
| 2003/0220691 A1 * | 11/2003 | Songer et al. | 623/17.14 |
| 2007/0233272 A1 * | 10/2007 | Boyce et al. | 623/23.63 |

* cited by examiner

PROSTHETIC DISC AND VERTEBRAL BODY REPLACEMENT DEVICE HAVING PYROLYTIC CARBON BEARING MEMBERS

FIELD OF THE INVENTION

The present invention relates to prosthetic devices. More particularly, the present invention relates to a spinal motion device for implanting in the disc space of the spine or as an artificial bone or bone segment, wherein the device has one or more bearing members made of pyrolytic carbon.

BACKGROUND OF THE INVENTION

A large segment of the population have chronic back and neck problems which cause pain and disability. The cause of the pain is often due to irritation of nerves, nerve roots or the spinal cord itself. This irritation can be caused by both chemical and mechanical processes. For example, nuclear material from the disc has been shown to irritate nerve cells. Also, pressure, resulting from contact with adjacent tissue can also be applied directly and induce pain in nerve tissues. A second cause of pain is believed to be degeneration of the disc material that lies between two adjacent vertebrae. Degeneration can result in pain directly, or it can lead to abnormal motions which result in pain.

Surgical techniques have been developed to eliminate the cause of the persistent pain either by clearing space around the nerves, nerve roots or spinal cord (so called decompressions) or by removing the disc and filling the space. The space filler can be a device that prevents motion (fusion) or can be a device that permits motion, preferably in a physiologic way. In some decompressive cases, it is necessary to remove part of the vertebral body and the adjacent discs.

Known prosthetic discs are typically designed to allow for some motion between the adjacent vertebrae. However, these known devices typically require resection of some limited amount of bone so as to obtain fixation. This is problematic for both the cases of true disc degeneration, and for many decompressive cases. In true disc degeneration, the disc is the source of pain and its removal is required, not the bone of the adjacent vertebral bodies. Removal of the bone, through a variety of instruments, can be surgically difficult and typically removes the densest cancellous bone in the vertebral body, thereby weakening the reconstruction. In decompressive cases where a portion of the vertebral body must be removed, the existing prosthetic devices are not designed to fit the void space created by the decompression. Devices that fit the space do not permit motion between the replaced vertebral body and adjacent vertebral bodies.

Accordingly, a spinal motion device is needed which permits either replacement of the disc without bone removal or that permits partial resection of the bone and still restores motion.

SUMMARY OF THE INVENTION

In summary, the present invention is a spinal motion device for implanting in the spine as a replacement for the natural disc, to permit motion between the two adjacent vertebral bodies or as a vertebral body replacement that permits motion at its ends. The device comprises a body having opposing first and second surfaces, and at least a first bearing member attached to the first support surface.

In one aspect of the invention, the device further comprises a second bearing member attached to the second surface.

In a further aspect of the invention, one or both of the bearing members are made of pyrolytic carbon.

In another aspect of the present invention, the device can be made in different sizes by changing the distance between the support surfaces to allow the device to function as a disc replacement or as a vertebral body replacement.

BRIEF DESCRIPTION OF THE DRAWINGS

FIG. 9 is an exploded anterior elevational view of the motion device of FIG. 7.

The drawings use like numerals to identify like elements. It should be understood that the drawings are for purposes of illustrating the concepts of the invention and are not necessarily to scale.

DETAILED DESCRIPTION OF THE INVENTION

Figure 1:
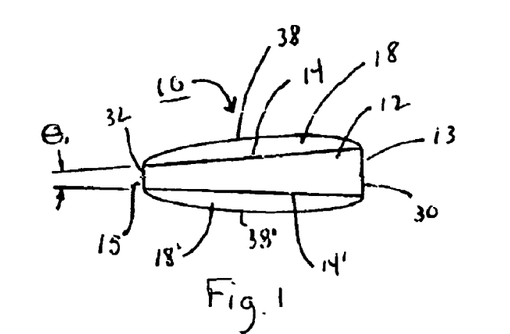
FIG. 1 is a side elevational view of a motion device according to a first illustrative embodiment of the present invention.
Figure 2:
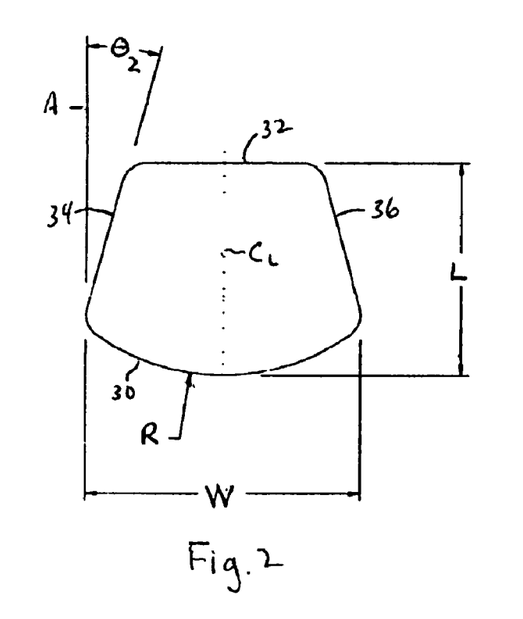
FIG. 2 is a plan view of the motion device of FIG. 1.
Figure 3:
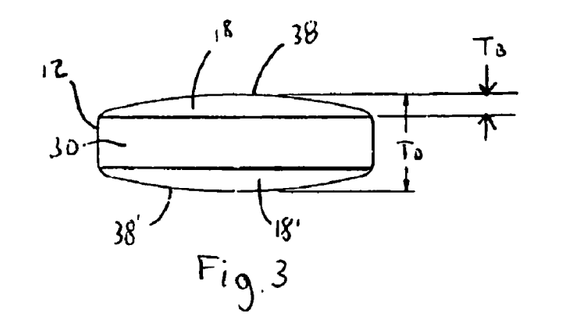
FIG. 3 is an anterior end view of the motion device of FIG. 1.

FIGS. 1-3 collectively show a spinal motion device 10 according to an illustrative embodiment of the present invention. The motion device 10 has a composite structure comprised of a porous body 12 and at least a one bearing member 18. The motion device 10 typically has a wedge-shape, side profile that tapers down from an anterior end face 30 toward a posterior end face 32. The embodiment of the device 10 shown in FIGS. 1-3, has a symmetrical taper, however, the device 10 may be also be asymmetrically tapered. The motion device 10 is intended as a replacement for the natural disc, to permit motion between the two adjacent vertebral bodies or as a vertebral body replacement that permits motion at its ends.

The body 12 of the device 10 may symmetrically or asymmetrically taper down from an anterior end 13 toward a posterior end 15. The angle 01 of this taper may be 6.8 degrees as measured between a first bearing support surface 14 and a second bearing support surface 14' of the body 12. The first bearing member 18 is attached to the first bearing support surface 14 of the body 12 and, in the embodiment of FIGS. 1-3, a second bearing member 18' is attached to the second bearing support surface 14' of the body 12.

Alternatively, the porous body 12 of the motion device 10 may have support surfaces that are generally parallel and bearing members constructed to provide the device with a posteriorly directed taper. In applications relating, for example, to the thoracic spine, the motion device may not to have a posteriorly directed taper or may be constructed such that the device has an anteriorly directed taper.

The porous body 12 is preferably made from a porous material. One example is the porous metal material available under the tradename HEDROCEL® from the Implex Corporation, the assignee herein. This material mimics the microstructure of natural cancellous bone and is described in detail in U.S. Pat. No. 5,282,861 entitled "OPEN CELL TANTALUM STRUCTURES FOR CANCELLOUS BONE IMPLANTS AND CELL AND TISSUE RECEPTORS" issued to R. B. Kaplan, the entire disclosure of which is incorporated herein by reference. This material consists of a three dimensional network of pores which form continuous, uniform channels with no dead ends. The material has a much lower modulus than a pure metallic implant, and has a significantly better pore size and shape distribution than prior art materials. This intricate network of interconnected pores provides optimal permeability and a high surface area to encourage tissue ingrowth, vascularization, and deposition of new bone, while also allowing for the interdigitation of bone cement for those situations that require it.

The bearing members 18, 18' can be made from a biocompatible material or combination of biocompatible materials. Such materials may include biocompatible metals, metal alloys, ceramics, and polymers. Preferably, the bearing members 18, 18' are made from a graphite and pyrolytic carbon composite (pyrolytic carbon). Pyrolytic carbon is preferred due to its excellent capabilities to articulate against cartilage (see, for example, "Wear Characteristics Of The Canine Acetabulum Against Different Femoral Prostheses" Cook et al., The Journal Of Bone And Joint Surgery, vol. 71-B, No. 2, pp. 189-197, March 1989). Pyrolytic carbon is typically made by machining a graphite substrate to have a geometry similar to, but smaller than, the desired final size of the part. The graphite is then placed in a fluidized or rotating bed reactor. The bed and graphite parts are heated to between 1,200 and 1,500 degrees C. and then a hydrocarbon is introduced in the bed. The hydrocarbon undergoes pyrolysis and pyrolytic carbon is deposited on the substrate. Processes for making pyrolytic carbon are well known in the art. For example, a process for making pyrolytic carbon is described in detail in U.S. Pat. No. 6,410,087.

As shown in FIGS. 1 and 2, the body 12 generally forms the anterior and posterior end faces 30 and 32 of the motion device 10. The posterior end face 32 is planar, and the anterior end face 30 is convexly curved, to substantially match the shape of the anterior portion of the outer edge of the vertebra. The body 12 also forms a planar, first side face 34 and an opposed, planar, second side face 36 that convergingly extend from the anterior end face 30 to the posterior end face 32, such that each of the side faces 34, 36 is disposed at angle 02 that may be about 15 degrees as measured from imaginary line A, which is parallel to the center line CL of the device 10. The angulation prevents the motion device from moving posteriorly into the spinal cord. Further, when the device 10 is used as a vertebral body replacement, the planar side faces 34, 36 allow the surgeon to easily cut the bone flat using an oscillating saw or osteotome or similar instrument.

For cervical replacement applications, the width W of the device 10 as measured between the junctions of the side faces 34, 36 and the anterior end face 30 may range between about 0.433 inches and about 0.551 inches. The length L of the device 10 as measured between anterior face and the posterior face at the center line CL of the device 10, may range between 0.39 inches and about 0.55 inches. The thickness TD of the device 10 (FIG. 3) as measured at the anterior end face 30, may range between 0.118 inches and 1.50 inches. The convexly curved anterior end face 30 may have a radius R of about 4.33 inches. One of ordinary skill in the art will of course recognize that the device 10 can be constructed in a different shapes and dimensions for other applications.

Referring still to FIGS. 1-3, the bearing members 18, 18' of the motion device 10 define a pair of spaced apart, bearing surfaces 38, 38' which extend between the anterior face 30 and the posterior face 32, and between the first side face 34 and the second side face 36. The bearing members 18, 18' may each have a profile, which when viewed in plan, is substantially identical to the plan profile of the body 12. The bearing surfaces 38, 38' may convexly curve in an elliptical and/or spherical manner in any one or all of a plurality of directions. In the embodiment shown in FIGS. 1-3, the bearing surfaces 38, 38' each convexly curves in an elliptical manner from the anterior face 30 to the posterior face 32, and convexly curves in an elliptical manner from the first side face 34 to the second side face 36. One of ordinary skill in the art will of course appreciate that one or both bearing members 18 may be formed with other bearing surface configurations including but not limited to concavely curved bearing surfaces and planar bearing surfaces.

Figure 4A:
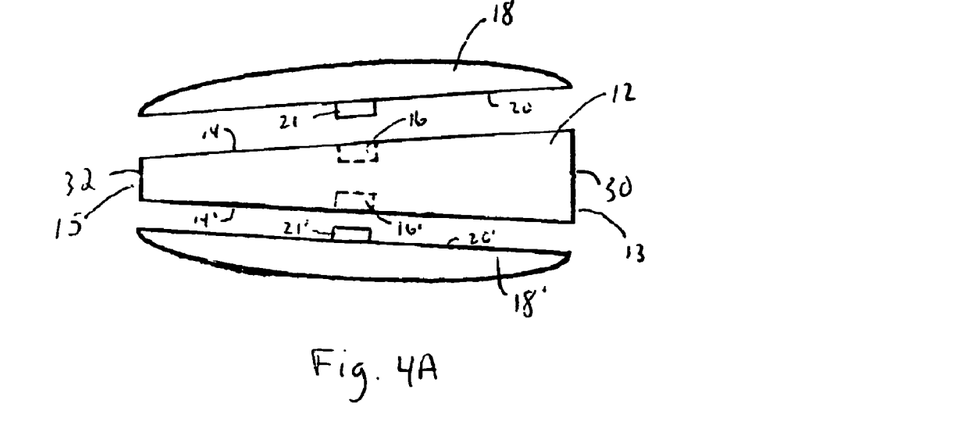
FIGS. 4A-4C are side elevational views of three different types of mechanical attachment arrangements that may be utilized in the motion device of the present invention.

Attachment of the bearing members 18, 18' to the body 12 can be accomplished using a variety of means. For example, mechanical means in the form of a post and hole press-fit arrangement may be utilized to attach the bearing members 18, 18' to the body 12. As shown in FIG. 4A, the post and hole arrangement may include at least one hole 16, 16' provided in each of the support surfaces 14, 14' of the body 12 and at least one post 21, 21' extending from each of the body mating surfaces 20, 20' of the bearing members 18, 18'. The holes 16, 16' and the posts 21, 21' may be dimensioned in a manner which creates a press-fit therebetween, thus mechanically retaining the bearing members 18, 18' to the body 12.

Figure 4B:
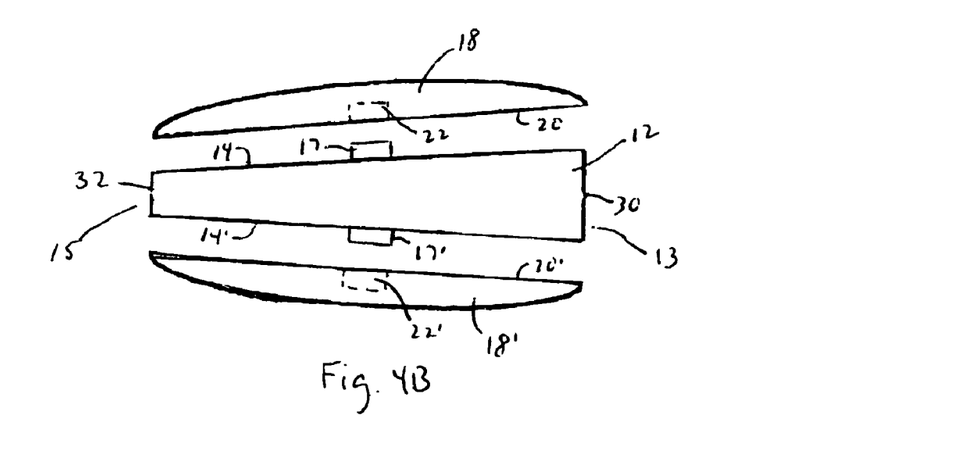

Alternatively, as shown in FIG. 4B, the post and hole arrangement may include at least one hole 22, 22' in each of the mating surfaces 20, 20' of the bearing members 18, 18' and at least one post 17, 17' extending from each of the support surfaces 14, 14' of the body 12.

Figure 4C:
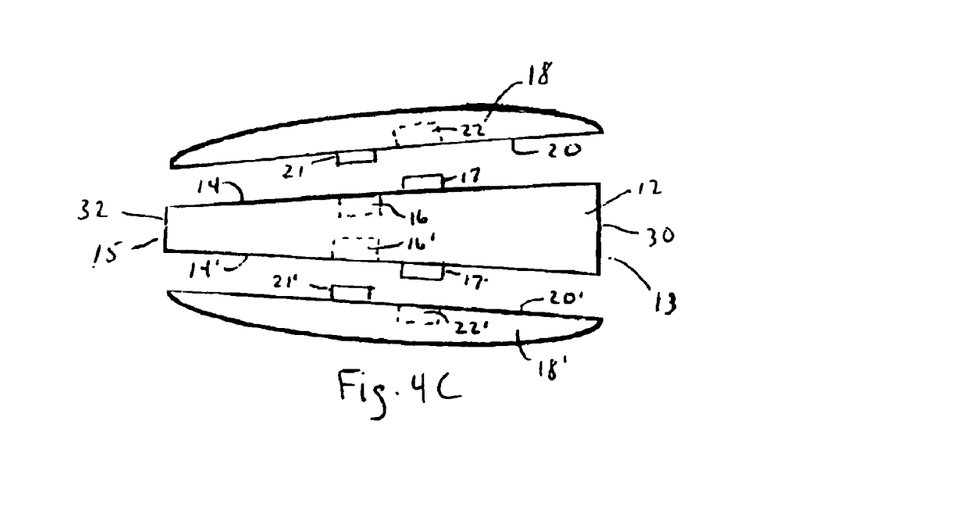

In addition, as shown in FIG. 4C, the post and hole arrangement may include at least one hole 16, 16' in each of the support surfaces 14, 14' of the body 12 and at least one post 17, 17' extending from each of the support surfaces 14, 14' of the body 12, and at least one hole 22, 22' in each of the mating surfaces 20, 20' of the bearing members 18, 18' and at least one post 21, 21' extending from each of the mating surfaces 20, 20' of the bearing members 18, 18'.

To further ensure attachment of the bearing members 18, 18' to the body 12, a grout in the form of a cement or a resilient polymer may be applied to the support surfaces 14, 14' of the body 12 and the mating surfaces 20, 20' of the bearing members 18, 18'. The grout may also be applied to the surfaces of the holes 16, 16', 22, 22', and the surfaces of the posts 17, 17', 21, 21'. Suitable grout materials include polyethylene, polymethylmethacrylate (PMMA), polyurethanes, polycarbonate urethanes, sand resilient polymers such as hydrogels, silicones, urethanes and siloxane-urethanes. When grout is utilized, the holes 16, 16', 22, 22', and the posts 17, 17', 21, 21' are dimensioned in a manner which create a gap therebetween, the gap being filled by the grout material, thus mechanically retaining the bearing members 18, 18' to the body 12. One advantage of using a resilient polymer grout between the bearing members 18, 18' and the body 12 is that it provides a slight cushioning effect between the bearing members 18, 18' and the body 12, which enables the device 10 to simulate the compliance of the normal disc.

Figure 5:
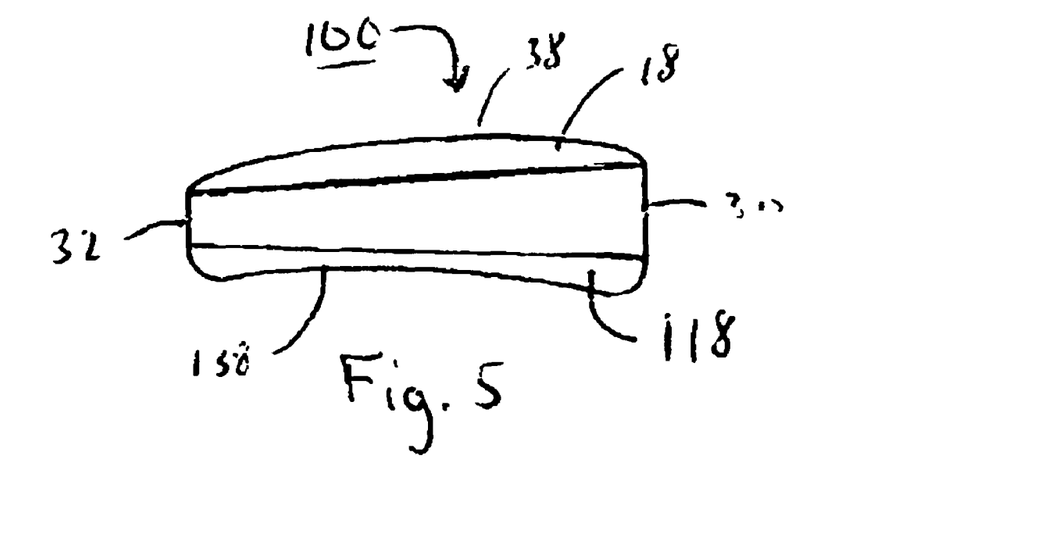
FIG. 5 is a side elevational view of a motion device according to a second illustrative embodiment of the present invention.
Figure 6:
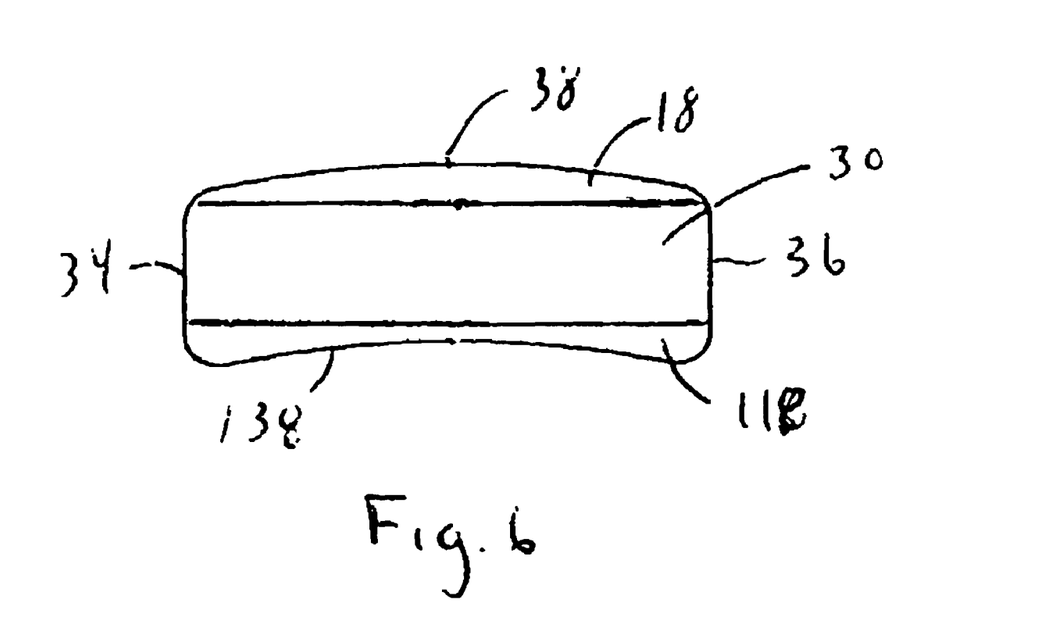
FIG. 6 is an anterior end view of the motion device of FIG. 5.

FIGS. 5 and 6 collectively show a motion device 100 according to a second illustrative embodiment of the present invention. In this embodiment, the bearing member denoted by numeral 118 defines a concave bearing surface 138 (the other bearing member 18 is substantially identical to the previous embodiment of FIGS. 1-3 with a convex bearing surface 38). The convex bearing surface 38 and the concave bearing surface 138 both extend between the anterior face 30 and the posterior face 32, and between the first side face 34 and the second side face 36. The convex bearing surface 38 may convexly curve in an elliptical and/or spherical manner as described earlier, and the concave bearing surface 138' may concavely curve in an elliptical and/or spherical manner. The bearing members 18 and 118 are also preferably made from the earlier described graphite and pyrolytic carbon composite material and may be attached to the porous body 12 using the methods described above.

As shown in FIGS. 5 and 6, the convex bearing surface 38 convexly curves in an elliptical manner from the anterior face 30 to the posterior face 32, and convexly curves in an elliptical manner from the first side face 34 to the second side face 36. The concave bearing surface 138 concavely curves in an elliptical manner from the anterior face 30 to the posterior face 32, and concavely curves in an elliptical manner from the first side face 34 to the second side face 36. As in the first embodiment, because the porous body 12 tapers down from the anterior end 13 toward the posterior end 15, the motion device 100 has a wedge-shape, side profile that tapers down from the anterior face 30 toward the posterior face 32.

The motion device 100 shown in FIGS. 5 and 6 cal be used as a prosthetic device to replace the disc in cases where the endplate of one of the vertebral bodies is concave and the other is convex. Additionally, as a vertebral body replacement, the motion device shown in FIGS. 5 and 6 can be used in combination with the motion device shown in FIGS. 1-3 to replace two vertebral bodies, and to permit pyrolytic carbon on pyrolytic carbon articulation between the two vertebral body replacement devices.

Figure 7:
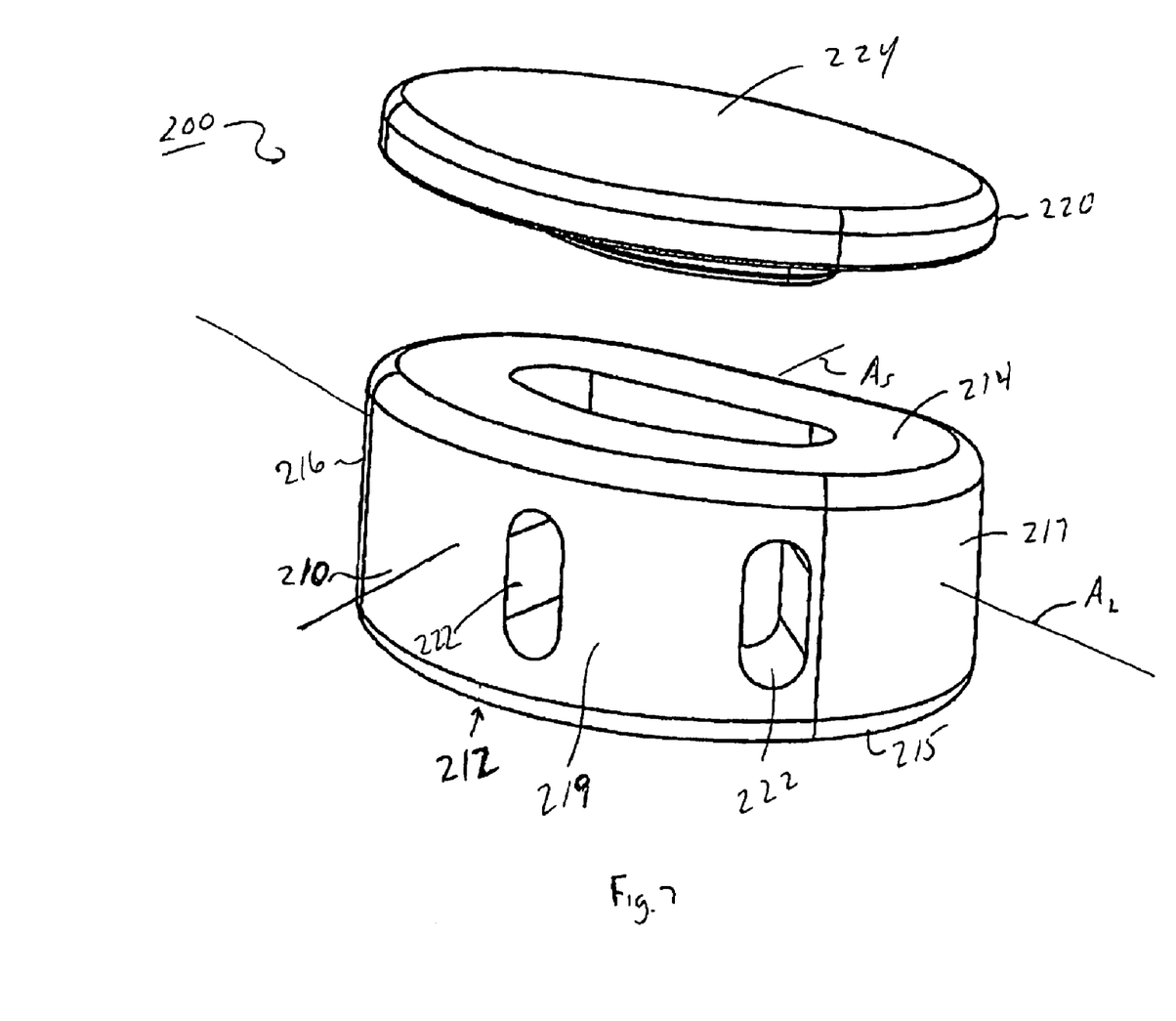
FIG. 7 is an exploded perspective view of a motion device according to a third illustrative embodiment of the present invention.
Figure 8:
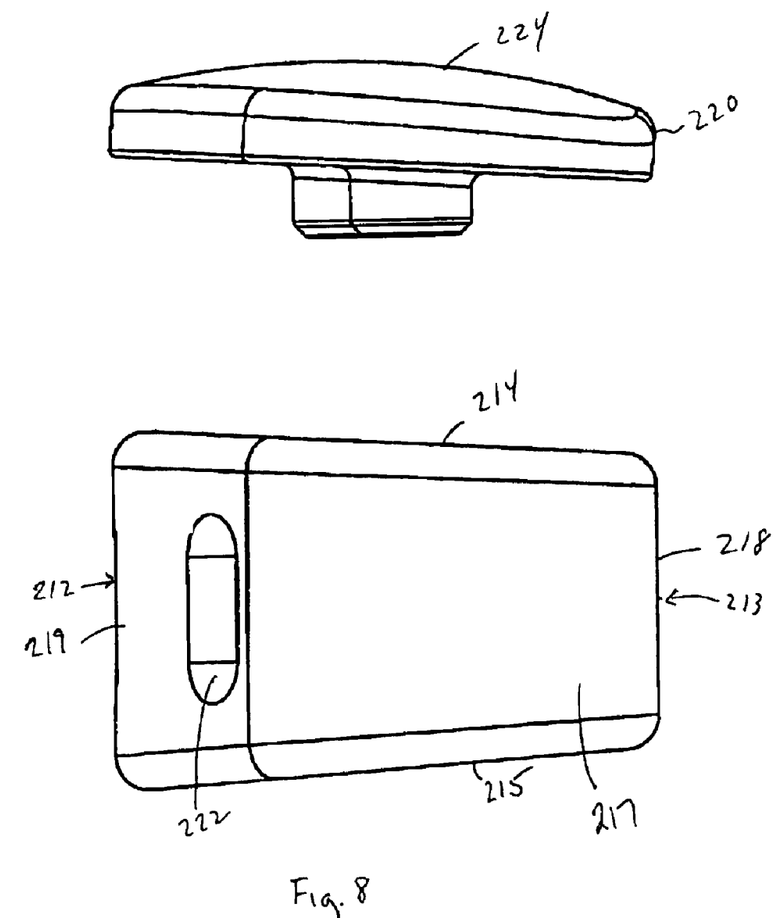
FIG. 8 is an exploded side elevational view of the motion device of FIG. 7.

FIGS. 7-9 collectively show a motion device 200 according to a third illustrative embodiment of the present invention. This motion device 200 is intended for use in the lumbar spine as a disc replacement. The porous body 210 of motion device 200 may be configured with a short axis As that extends in an anterior-posterior direction, and a long axis AL that extends perpendicular to the short axis As. The body 210 may symmetrically or asymmetrically taper down from the anterior end 212 toward the posterior end 213. A single bearing member 220, preferably made from the earlier described graphite and pyrolytic carbon composite material, attaches to bearing support surface 214 of the body 212 as described previously. The bearing member 220 may have a profile, which when viewed in plan, is substantially identical to the plan profile of the body 210. The bearing member 220 further includes a bearing surface 224 that may convexly curve in an elliptical and/or spherical manner in any one or all of a plurality of directions. One of ordinary skill in the art will of course appreciate that the bearing member 220 may be formed with other bearing surface configurations including but not limited to concavely curved bearing surfaces and planar bearing surfaces.

Still referring to FIGS. 7-9, the bearing support surface 214 and opposing surface 215 of the body 212 are separated by convexly curved side surfaces 216, 217, which extend between truncated posterior end face 218 and convex anterior end face 219. The convexly curved shape of the side faces 216, 217 and anterior end face 219 mimic the overall of the vertebral bodies. One or more apertures 222 are provided in the anterior convex end face 219 for enabling the device 200 to be inserted in the lumbar spine with a conventional insertion instrument (not shown).

While the foregoing invention has been described with reference to the above embodiments, various modifications and changes can be made without departing from the spirit of the invention. Accordingly, all such modifications and changes are considered to be within the scope of the appended claims.

What is claimed is:

1. A spinal motion device comprising:
   a body having opposing first and second surfaces, the body made from an artificial bone material; and
   at least a first bearing member attached to the first surface, the at least first bearing member comprising a graphite and pyrolytic carbon composite.

2. The device of claim 1, wherein the body is porous.

3. The device of claim 1, wherein the first and second surfaces are separated by side surfaces which extend between a posterior end of the body and an anterior end of the body.

4. The device according to claim 1, wherein the first and second surfaces taper posteriorly such that the body has a thickness that decreases from the anterior end to the posterior end.

5. The device according to claim 1, wherein the at least first bearing member defines a convex bearing surface.

6. The device according to claim 1, wherein the at least first bearing member defines a bearing surface that convexly curves in an elliptical manner.

7. The device according to claim 1, further comprising a second bearing member attached to the second surface.

8. The device according to claim 7, wherein the second bearing member comprises a graphite and pyrolytic carbon composite.

9. The device according to claim 7, wherein the first bearing member defines a convex bearing surface.

10. The device according to claim 9, wherein the second bearing member defines a concave bearing surface.

11. The device according to claim 1, further comprising a post and hole arrangement associated with the at least first bearing member and the body for attaching the bearing member to the first surface of the body.

12. The device according to claim 11, further comprising a grout for aiding the post and hole arrangement in attaching the at least first bearing member to the first surface of the body.

13. The device according to claim 12, wherein the grout comprises one of a cement and a polymer.

14. The device according to claim 13, wherein the polymer is selected from the group consisting of polyethylene, urethane, silicone, siloxane-urethane, polyurethane, polycarbonate urethane, and hydrogel.

15. The device according to claim 13, wherein the polymer is resilient.

16. The device according to claim 1, further comprising a grout for attaching the at least first bearing member to the first surface of the body.

17. The device according to claim 16, wherein the grout comprises one of a cement and a polymer.

18. The device according to claim 17, wherein the polymer is selected from the group consisting of polyethylene, urethane, silicone, siloxane-urethane, polyurethane, polycarbonate urethane, and hydrogel.

19. The device according to claim 17, wherein the polymer is resilient.

20. The device according to claim 1, wherein the device is useable as a disc replacement or as a vertebral body replacement.

21. The device according to claim 1, wherein the at least first bearing member defines a concave bearing surface.

22. A spinal motion device for implanting in a spine, the device comprising:
   a porous body having opposing first and second surfaces, the body made from an artificial bone material;
   a first bearing member comprising a graphite and pyrolytic carbon composite, and combinations thereof; and
   attaching means for attaching the first bearing member to the first surface.

23. The device according to claim 22, further comprising:
   a second bearing member comprising a biocompatible material selected from the group consisting of polymers, graphite and pyrolytic carbon composites, and combinations thereof;
   and attaching means for attaching the second bearing member to the second surface.

* * * * *